US012698484B2

(12) United States Patent
Huang et al.

(10) Patent No.: US 12,698,484 B2
(45) Date of Patent: Aug. 4, 2026

(54) ω-TRANSAMINASE MUTANT BASED ON ANCESTRAL SEQUENCE RECONSTRUCTION

(71) Applicant: ZHEJIANG UNIVERSITY OF SCIENCE & TECHNOLOGY, Hangzhou (CN)

(72) Inventors: Jun Huang, Hangzhou (CN); Tingting Cai, Hangzhou (CN); Shui Qiu, Hangzhou (CN); Lehe Mei, Hangzhou (CN); Jiaren Cao, Hangzhou (CN); Changjiang Lyu, Hangzhou (CN); Fangfang Fan, Hangzhou (CN); Sheng Hu, Hangzhou (CN); Ye Li, Hangzhou (CN); Weirui Zhao, Hangzhou (CN); Feng Wang, Hangzhou (CN); Yuanyuan Li, Hangzhou (CN)

(73) Assignee: ZHEJIANG UNIVERSITY OF SCIENCE & TECHNOLOGY, Hangzhou (CN)

( * ) Notice: Subject to any disclaimer, the term of this patent is extended or adjusted under 35 U.S.C. 154(b) by 430 days.

(21) Appl. No.: 18/287,879

(22) PCT Filed: Dec. 5, 2022

(86) PCT No.: PCT/CN2022/136528
§ 371 (c)(1),
(2) Date: Oct. 21, 2023

(87) PCT Pub. No.: WO2023/103947
PCT Pub. Date: Jun. 15, 2023

(65) Prior Publication Data

US 2025/0304928 A1 Oct. 2, 2025

(30) Foreign Application Priority Data

Dec. 7, 2021 (CN) ........................ 202111482472.1

(51) Int. Cl.
*C12N 9/10* (2006.01)
*C12P 7/26* (2006.01)

(52) U.S. Cl.
CPC .............. *C12N 9/1096* (2013.01); *C12P 7/26* (2013.01); *C12Y 206/01018* (2013.01)

(58) Field of Classification Search
CPC ........ C12N 9/1096; C12P 7/26; C12P 13/001; C12Y 206/01018; C12Y 206/01
See application file for complete search history.

(56) References Cited

FOREIGN PATENT DOCUMENTS

| | | |
|---|---|---|
| CN | 104480155 | 4/2015 |
| CN | 108913671 | 11/2018 |
| CN | 110144335 | 8/2019 |
| CN | 112359030 | 2/2021 |
| CN | 112481230 | 3/2021 |

OTHER PUBLICATIONS

Huang (CN 12481230) translation retrieved Jan. 28, 2026 from PatentScope at https://patentscope.wipo.int/search/en/detail.jsf?docId=CN320958472&_cid=P11-MKYKW4-10312-1 (Year: 2026).*

* cited by examiner

*Primary Examiner* — Louise W Humphrey
(74) *Attorney, Agent, or Firm* — Jiwen Chen; Joywin IP Law PLLC

(57) ABSTRACT

The amino acid sequence of a w-transaminase mutant derived from mutation of ω-transaminase from *Aspergillus terreus*, is as shown in SEQ ID NO. 4 or SEQ ID NO. 6. Compared with the wild-type enzyme, the half-lives of the ω-transaminase mutants are all above 24 h, while the half-life of the wild-type is only 6.90 min. The half-inactivation temperature of the mutants are 49.00° C. and 49.03° C., respectively, which are about 11° C. higher than that of the wild-type (37.89° C.), such that the thermal stability is significantly improved.

7 Claims, 4 Drawing Sheets

Specification includes a Sequence Listing.

a b a b

ω-TRANSAMINASE MUTANT BASED ON ANCESTRAL SEQUENCE RECONSTRUCTION

This is a U.S. national stage application of PCT Application No. PCT/CN2022/136528 under 35 U.S.C. 371, filed Dec. 5, 2022 in Chinese, claiming priority of Chinese Application No. 202111482472.1, filed Dec. 7, 2021, all of which are hereby incorporated by reference.

FIELD OF TECHNOLOGY

The present invention relates to the technical field of molecular biology, specifically to an ω-transaminase mutant based on ancestral sequence reconstruction.

BACKGROUND TECHNOLOGY

Chiral amines are a class of compounds containing amino groups in the chiral centers of small molecule compounds, which are an important class of intermediates for drug synthesis. In recent years, with the expansion of chiral drug market, chiral amines and their derivatives comprise over 70% of the share of chiral drugs, such as neurological drugs, cardiovascular drugs, anti-hypertensive drugs, anti-infective drugs and vaccines, etc.; sitagliptin, the main ingredient of anti-diabetic drugs, is an R-type amine. The huge market demand for chiral amine drugs makes the efficient preparation of chiral amine drugs extremely important.

Aminotransferase is a key enzyme for preparing chiral amines by biological method, which can reversibly catalyze the amino transfer reaction between ketone and amino groups to synthesize amine compounds. The ω-transaminase from *Aspergillus terreus* uses pyridoxal phosphate (PLP) as a co-enzyme to catalyze transfer of amino groups from an amino group donor to a ketone acceptor to produce chiral amines and by-product ketones, as shown in the following catalytic process:

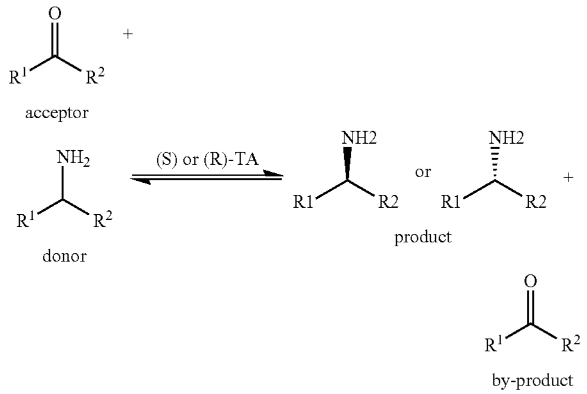

Although transaminases have promising applications in the synthesis of chiral amines, wild-type enzymes have many deficiencies in terms of substrate specificity, stability and catalytic efficiency, which are not beneficial to their industrial application. The half-life of wild-type ω-transaminase derived from *Aspergillus terreus* is only 6.90 min at 40° C., which needs modification for thermal stability. The patent applications CN105441404A and CN105950581A modified wild-type ω-transaminases utilizing targeted mutation technology and obtained ω-transaminase mutants with further improved thermal stability. With the continuous development of computer technology, obtaining ancestral enzymes with better thermal stability by ancestral sequence reconstruction technique has also become a research hotspot.

Ancestral sequence reconstruction (ASR) is a technique to derive amino acid sequences of ancestral enzymes of extinct organisms by computer algorithms. Based on the assumption that the Earth's environment during the Precambrian period was extreme, such as high temperatures, and that primitive cells relied on only a few enzyme lines, it is generally assumed that ancestral enzymes usually have better thermal stability. Thus, using ancestral sequence reconstruction technique to obtain ancestral enzymes of existing enzymes has also become a method to improve thermal stability and activity of enzymes, such as Hendrikse et al. (Yosephin Gumulya, et al. Engineering highly functional thermostable proteins using ancestral sequence reconstruction. *Nature Catalysis,* 2018, 1(11): 878-888) used ancestral enzyme sequence reconstruction technique to improve stability and activity of bacterial diterpenoid cyclases; Risso Valeria et al. (Risso Valeria A, et al. Hyperstability and substrate promiscuity in laboratory resurrections of Precambrian β-lactamases. *Journal of the American Chemical Society,* 2013. (135(8): 2899-902) obtained β-lactamases that are more heat resistant than existing enzymes by ASR techniques.

No relevant studies have been reported on the use of ancestral sequence reconstruction technique to obtain ancestral enzymes of existing enzymes to improve the thermal stability of *Aspergillus terreus* ω-transaminase.

SUMMARY OF INVENTION

The present invention is based on a method of obtaining ancestral enzymes of existing enzymes utilizing ancestral sequence reconstruction technique, by which *Aspergillus terreus* ω-transaminase mutants with further improved enzyme activity and thermal stability are obtained.

The present invention uploaded the protein sequence of *Aspergillus terreus* ω-transaminase to Fire ProtASR, a server for fully automated ancestral sequence reconstruction), and by the fully automated analysis provided by this website a phylogenetic tree of *Aspergillus terreus* ω-transaminase was obtained, then respective nodes on the branch of the phylogenetic tree of evolving to *Aspergillus terreus* ω-transaminase were selected, the gene sequences corresponding to these nodes were downloaded from this website, and then the corresponding post-mutation gene sequences were obtained by full gene synthesis. After enzyme expression, purification and thermal stability assay, two mutants with significantly improved thermal stability were finally obtained:

Mutant 1, Named as Ancata-101:

D5E-A12Q-I17V-S20A-T21S-E22A-T23S-A42H-I77L-T78S-T85S-L87M-R90K-D96E-Q97E-E104D-T130S-R131K-D134E-I135L-138insN-V143I-D153E-V157T-V162I-V163I-A174S-I175M-V188T-A195S-H210N-Q236E-N245D-A246V-E248R-F250N-F258V-R266Q-T284S-M288K-G292D-Q294K-I295V-A313P-N322E-E323S-R324A-N325S-325insKKSG;

Mutant 2, Named as Ancata-124:

D5E-A12Q-I17V-S20A-T21S-E22A-T23S-A42H-I77L-T78S-T85A-R90K-D96E-Q97E-E104D-T130S-R131K-I135L-138insN-V143I-D153E-M154V-V157T-V162I-V163I-A195S-H210N-Q236E-N245D-A246V-E248R-F250N-F258V-L263M-R266Q-T284S-

M288K-G292D-Q294 K-I295V-A313P-N322E-E323S-R324A-N325S-325insKS, in which 138insN means inserting N (asparagine) after position 138 of the amino acid sequence of the wild-type enzyme; 325insKKSG means inserting KKSG (K: lysine, S: serine, G: glycine) after position 325 of the amino acid sequence of the wild-type enzyme; 325insKS means inserting KS after position 325 of the amino acid sequence of the wild-type enzyme.

The present invention provides an ω-transaminase mutant based on ancestral sequence reconstruction, the ω-transaminase mutant is derived from mutation of ω-transaminase from *Aspergillus terreus*, the wild-type ω-transaminase has an amino acid sequence as shown in SEQ ID No. 2, and the ω-transaminase mutant has an amino acid sequence as shown in SEQ ID NO. 4 or SEQ ID NO. 6.

The present invention further provides the use of said ω-transaminase mutant in catalyzing generation of acetophenone from (R)-(+)-α-methylbenzylamine. Compared to the wild-type enzyme, the mutant enzyme has better thermodynamic stability at higher temperatures and is more suitable for industrial applications.

The present invention further provides genes encoding the ω-transaminase mutants.

Preferably, the gene sequences of the two ω-transaminase mutants are shown in SEQ ID NO. 3 and SEQ ID NO. 5.

The present invention further provides the use of the genes in catalyzing generation of acetophenone from (R)-(+)-α-methylbenzylamine.

The present invention also provides recombinant expression plasmids comprising the above genes.

The present invention also provides genetically engineered bacteria comprising the above recombinant expression plasmids.

The present invention also provides the use of the above genetically engineered bacteria in catalyzing generation of acetophenone from (R)-(+)-α-methylbenzylamine.

The present invention also provides a method for catalyzing generation of acetophenone from (R)-(+)-α-methylbenzylamine, where acetophenone is generated by a transamination reaction using (R)-(+)-α-methylbenzylamine and pyruvic acid as substrates and catalyzed by the above ω-transaminase mutants or the above genetically engineered bacteria.

Compared with the prior art, the present invention has the following beneficial effects:

(1) Compared with the wild-type enzyme, the half-lives of the ω-transaminase mutants are all above 24 h, while the half-life of the wild-type is only 6.90 min. The half-inactivation temperature of the mutants are 49.00° C. and 49.03° C., respectively, which are about 11° C. higher than that of the wild-type (37.89° C.), such that the thermal stability is significantly improved.

(2) Using ancestral sequence reconstruction technique, we screen and obtain ω-transaminase mutants that are significantly better than the wild-type enzyme in terms of thermodynamic stability and enzyme activity.

DESCRIPTION OF THE EMBODIMENTS

Example 1

Figure 1:
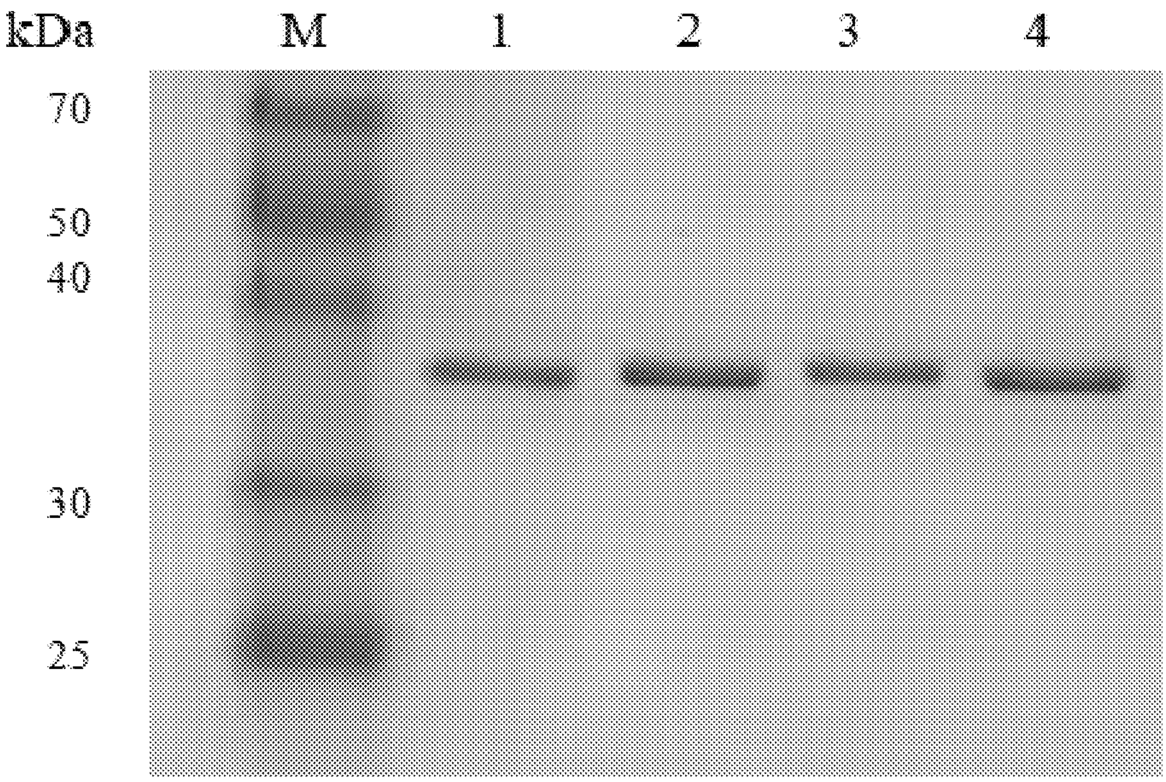
FIG. 1 is the electrophoresis analysis result of SDS-PAGE of wild-type and mutants; in which, each lane is M: protein marker; 1: wild-type enzyme solution (unpurified); 2: wild-type enzyme solution (purified); 3: mutant Ancata-101 enzyme solution (purified); 4: mutant Ancata-124 enzyme solution (purified), respectively.

The wild-type ω-transaminase from *Aspergillus terreus* has an amino acid sequence as shown in SEQ ID NO. 2, and has a gene sequence as shown in SEQ ID NO. 1.

The protein sequence of *Aspergillus terreus* ω-transaminase was uploaded to Fire ProtASR (https://loschmidt.chemi.muni.cz/fireprotasr/, a server for fully automated ancestral sequence reconstruction), and by the fully automated analysis through this website a phylogenetic tree of *Aspergillus terreus* ω-transaminase was obtained, then respective nodes on the branch of the phylogenetic tree of evolving to *Aspergillus terreus* ω-transaminase were selected, the gene sequences corresponding to these nodes were downloaded from this website, and then the corresponding post-mutation gene sequences were obtained by full gene synthesis. After enzyme expression, purification and thermal stability assay, two mutants with significantly improved thermal stability were finally obtained, named Ancata-101 and Ancata-124, whose mutation position and sequence are as follows:

Ancata-101:

D5E-A12Q-I17V-S20A-T21S-E22A-T23S-A42H-I77L-T78S-T85S-L87M-R90K-D96E-Q 97E-E104D-T130S-R131K-D134E-I135L-138insN-V143I-D153E-V157T-V162I-V163I-A174S-I175M-V188T-A195S-H210N-Q236E-N245D-A246V-E248R-F250N-F258V-R266Q-T284S-M 288K-G292D-Q294K-I295V-A313P-N322E-E323S-R324A-N325S-325insKKSG, Gene sequence as shown in SEQ ID NO. 3, amino acid sequence as shown in SEQ ID NO. 4;

Ancata-124:

D5E-A12Q-I17V-S20A-T21S-E22A-T23S-A42H-I77L-T78S-T85A-R90K-D96E-Q97E-E 104D-T130S-R131K-I135L-138insN-V143I-D153E-M154V-V157T-V162I-V163I-A195S-H210 N-Q236E-N245D-A246V-E248R-F250N-F258V-L263M-R266Q-T284S-M288K-G292D-Q294 K-I295V-A313P-N322E-E323S-R324A-N325S-325insKS, Gene sequence as shown in SEQ ID NO. 5, amino acid sequence as shown in SEQ ID NO. 6;

Example 2

(1) Materials and Reagents

Full genes of (R)-ω-TA and the mutants were synthesized by GENERAL Biosystems (Anhui) Corporation Limited, the vector was pET-28a(+), and the expression host strain was *E. coli* BL21(DE3); isopropyl-β-D-thiogalactoside (IPTG), kanamycin sulfate, pyrodoxal-5'-phosphate (PLP), and modified Bradford protein concentration assay kit were purchased from Sangon Biotech (Shanghai) Co., Ltd.; protein marker and Ni-NTA chromatography medium were purchased from TransGen Biotech Co., Ltd.; sodium dodecyl sulfate polyacrylamide gel electrophoresis (SDS-PAGE) gel preparation kit was purchased from Beijing CoWin Biotech Co., Ltd.; dimethyl sulfoxide (DMSO), pyruvic acid and (R)-α-methylbenzylamine were purchased from Shanghai Aladdin Biochemical Technology Co., Ltd.

(2) Enzyme Expression and Purification

10 μL of wild-type recombinant plasmid bacteria broth and mutant bacteria broth were inoculated into 5 mL of Luria-Bertani liquid medium (LB medium) containing a final concentration of 50 μg/mL Kanamycin and incubated for 12 hours at 37° C. and 200 rpm in a shaker. The bacterial broth was transferred to 200 mL of LB liquid medium containing a final concentration of 50 μg/mL Kanamycin at 2% inoculum (v/v) and cultured for another 2-3 hours at 37° C. and 200 rpm. When $OD_{600}$ reached 0.8, IPTG was added at a final concentration of 0.5 mM and protein expression was induced at 25° C. and 150 rpm. After 20 hours of induction, the bacteria were collected by centrifugation at 6000 rpm, 4° C.

Bacterial cells were washed once with 50 mM PBS buffer (50 mM sodium dihydrogen phosphate, 50 mM disodium hydrogen phosphate, 300 mM sodium chloride, pH 8.0) to remove residual culture medium and resuspended in the above PBS buffer. The bacterial cells were disrupted by homogenizer under ice bath conditions. The cell disrupting solution was centrifuged at 8000 rpm, 4° C. for 1 hour. The supernatant obtained was collected as crude enzyme solution containing ω-transaminase. Subsequently, the crude enzyme solution was filtered through a 0.45 μm filter membrane and the target protein was purified using a Ni-NTA affinity chromatography column.

Purification buffers are as follows:

20 mM imidazole washing buffer: 50 mM sodium dihydrogen phosphate, 300 mM sodium chloride, 20 mM imidazole, pH 8.0;

50 mM imidazole washing buffer: 50 mM sodium dihydrogen phosphate, 300 mM sodium chloride, 50 mM imidazole, pH 8.0;

250 mM imidazole eluting buffer: 50 mM sodium dihydrogen phosphate, 300 mM sodium chloride, 250 mM imidazole, pH 8.0.

Specific purification steps:

1) Equilibrating the Ni-NTA affinity chromatography column: washing the column for 3 column volumes with 20% (v/v) ethanol aqueous solution, deionized water and 20 mM imidazole washing buffer in sequence;
2) Sample loading: the crude enzyme solution was taken by syringe and filtered through 0.45 μm filter membrane, and the target protein with a tag of 6 histidine could bind to the packing material.
3) Washing: washing the column with the 20 mM imidazole washing buffer and 50 mM imidazole washing buffer for 3 column volumes each, and using Bradford's solution to test if the protein impurities were washed out;
4) Elution: rinsing the column with the 250 mM imidazole eluting buffer and collecting 5 mL filtrate.
5) Preserving the column: washing the column with 20 mM imidazole washing buffer, deionized water and 20% (v/v) ethanol aqueous solution in sequence for 3 column volumes each, and finally preserving the column in 20% (v/v) ethanol aqueous solution.

(3) Determination of Protein Content.

A modified Bradford protein concentration determination kit was used to establish a protein content standard curve to determine the concentration of the pure enzyme obtained from step (2) in Example 2, and the preparation steps of the protein standard curve were carried out with reference to the instructions. The molecular weight and purity of the purified protein were identified by SDS-PAGE method. Specific steps were as follows:

Preparation of the gel: 12% separation gel, 5% concentration gel. The formulation is as shown in Table 1.

TABLE 1

Formulation of separation gel and concentration gel for SDS-PAGE protein electrophoresis

| mass fraction | 12% separation gel | 5% concentration gel |
|---|---|---|
| Volume (mL) | 5.00 | 2.00 |
| Double distilled water (mL) | 1.70 | 0.67 |
| 30% Acr-Bis (29:1) (mL) | 2.00 | 0.33 |
| Separation/concentration gel buffer (mL) | 1.25 | 1.00 |
| 10% Ammonium persulfate (mL) | 0.05 | 0.02 |
| TEMED (mL) | 0.003 | 0.002 |

Note:
Acr-Bis: Acrylamide-Bisacrylamide;
TEMED: N,N,N',N'-Tetramethylethylenediamine.

Sample processing: 40 μL of enzyme solution and 10 μL of 5× protein spiking buffer were mixed and kept in boiling water bath for 10 min.

Loading: protein marker 10 μL, sample 15 μL.

Electrophoresis conditions: electrophoresis runs at 120 V for about 90 min; stop the electrophoresis when bromophenol blue indicator is moved to about 1 cm from the lower edge of the gel.

Staining: The gel was covered by the staining solution, heated in microwave oven for 1 min and stained in shaker for 25 min.

Decolorization: The staining solution was recovered and replaced with decolorization solution, which was changed every hour until the protein bands were clear.

Protein content determination: The target protein was diluted to the linear range of the BSA standard curve, and the diluted protein concentration was obtained by measuring the A595 value by a microplate reader.

The SDS-PAGE electrophoresis profiles of the wild type and mutants are shown in FIG. 1. The electrophoretic bands of wild type and mutants were located at the same position and were consistent with the theoretical molecular weight of 36.1 kDa, which laid the foundation for subsequent experiments.

(4) Determination of Enzyme Activity

1) Determination of Enzyme Activity

20 μL of pure enzyme was reacted with 180 μL of substrate solution (10 mM PLP, 2.5 mM (R)-α-MBA ((R)-(+)-α-methylbenzylamine), 2.5 mM pyruvic acid, 0.25% DMSO, 50 mM PBS, pH 8.0) for 3 min at 25° C., and the production of $OD_{245}$ acetophenone was determined by reference to the literature (Rapid and sensitive kinetic assay for characterization of ω-transaminases. *Anal Chem,* 2009, 81: 8244-8248). Enzyme activity (U) was defined as the amount of enzyme required for transaminase to catalyze transamination reaction of the substrate pyruvic acid and (R)-α-MBA to produce 1 μmoL of acetophenone per minute under certain conditions.

Figure 2:
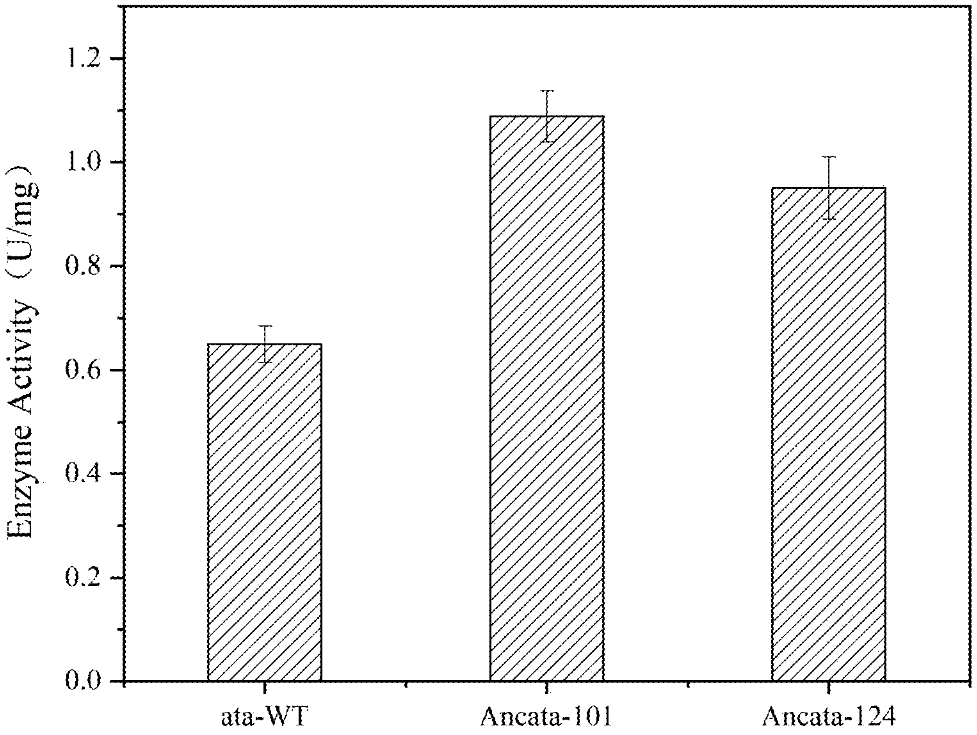
FIG. 2 is the result of enzyme activity assay for wild-type ω-transaminase and ω-transaminase mutant enzymes; in which, a is specific enzyme activity and b is relative enzyme activity.
Figure 2:
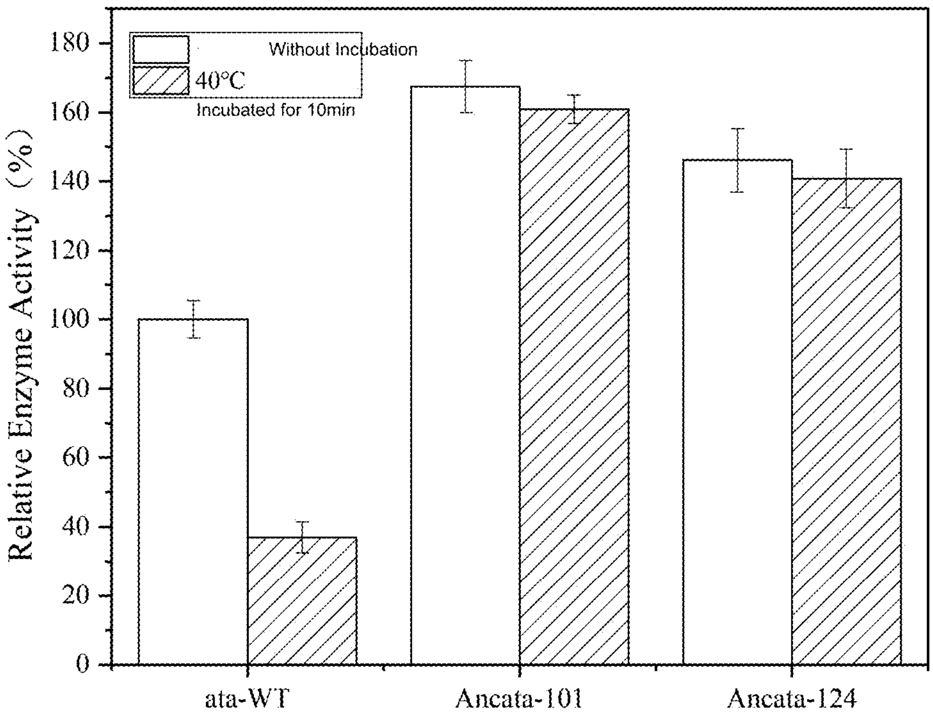

The enzyme activities of the wild type and two mutants are shown in FIG. 2(*a*). Compared with the enzyme activities of the wild type ω-transaminase, the enzyme activities of the two mutants were significantly higher, being 1.67 and 1.46 times of that of the wild type, respectively.

2) Determination of Residual Enzyme Activity

The purified wild-type and mutants were incubated at 40° C. for 10 min, and immediately cooled on ice for 10 min after incubation. Then, 20 μL of the heat-treated enzyme solution was reacted with 180 μL substrate solution (10 mM PLP, 2.5 mM (R)-α-MBA, 2.5 mM pyruvic acid, 0.25% DMSO, 50 mM PBS, pH 8.0) at 25° C. for 3 min. The residual activity of the wild type and mutants was determined. The experiments were performed in triplicates, and the enzyme activity of the wild type without incubation at 40° C. was set as 100%, and the mutants with higher relative enzyme activity than the wild type were screened. The residual activity of the wild type and the two mutants after heat treatment at 40° C. for 10 min is shown in FIG. 2(*b*). The activity of mutants Ancata-101 and Ancata-124 was basically undiminished, while that of the wild type decreased by about 60%.

In sum, using the ancestral sequence reconstruction method, two mutants with significantly enhanced thermal stability were screened. Ancata-101 (D5E-A12Q-I17V-S20A-T21S-E22A-T23S-A42H-I77L-T78S-T85S-L87M-R90K-D96E-Q97 E-E104D-T130S-R131K-D134E-I135L-138insN-V143I-D153E-V157T-V162I-V163I-A174S-I175M-V188T-A195S-H210N-Q236E-N245D-A246V-E248R-F250N-F258V-R266Q-T284S-M288K-G292D-Q294K-I295V-A313P-N322E-E323S-R324A-N325S-325insKKSG, Gene sequence as shown in SEQ ID NO. 3, amino acid sequence as shown in SEQ ID NO. 4); Ancata-124

(D5E-A12Q-I17V-S20A-T21S-E22A-T23S-A42H-I77L-T78S-T85A-R90K-D96E-Q97E-E104 D-T130S-R131K-I135L-138insN-V143I-D153E-M154V-V157T-V162I-V163I-A195S-H210N-Q236E-N245D-A246V-E248R-F250N-F258V-L263M-R266Q-T284S-M288K-G292D-Q294K-I 295V-A313P-N322E-E323S-R324A-N325S-325insKS, Gene sequence as shown in SEQ ID NO. 5, amino acid sequence as shown in SEQ ID NO. 6.

(5) Determination of Enzyme Kinetic Parameters

Different concentrations of 0, 0.125, 0.25, 0.5, 1.0, 1.5, 2.0, 2.5 and 3.0 mM (R)-α-MBA and pyruvic acid substrate solutions were respectively prepared with PBS buffer (50 mM, pH 8.0) containing 0.01 mM PLP. The enzyme activity of wild type and mutant ω-transaminase at different concentrations was determined by enzyme activity assay. The reaction rates V for different substrates as well as different substrate concentrations [S] were brought into the Michaelis-Menten equation $V=V_{max}\times[S]/(K_m+[S])$, nonlinear curve fit was performed using Origin 8.0 software, and the enzyme kinetic parameters $K_m$ and $V_{max}$ were calculated for wild type and mutants; the conversion number $k_{cat}$ and catalytic efficiency $k_{cat}/K_m$ were calculated for wild type and mutants from the equation $k_{cat}=V_{max}/[E]$, where [E] was the molar concentration of the enzyme. The results are shown in Table 2. The enhancement of conversion number of pyruvic acid by the two mutant enzymes was lower than the enhancement of affinity, and the catalytic efficiency was lower than that of the wild type for pyruvic acid. The $K_m^{\alpha\text{-}MBA}$ values of both mutant enzymes Ancata-101 and Ancata-124 were 0.28 mM, which were slightly higher than that of the wild type, but the $k_{cat}^{\alpha\text{-}MBA}$ value of Ancata-101 was 1.67 times higher than that of the wild type, while the $k_{cat}^{\alpha\text{-}MBA}$ value of Ancata-124 was slightly lower than that of the wild type. $k_{cat}/K_m^{\alpha\text{-}MBA}$ was calculated for Ancata-101 and Ancata-124, which were 3.81 $s^{-1}\cdot mM^{-1}$ and 2.07 $s^{-1}\cdot mM^{-1}$, respectively, and the catalytic efficiency of Ancata-101 for α-MBA was 1.35 times of the wild type, which was slightly enhanced, while the catalytic efficiency of Ancata-124 was lower than that of the wild type. Taken together, the catalytic efficiencies of the two mutants were not significantly enhanced.

TABLE 2

Kinetic parameters of wild type and mutants

| Name | WT-AT | Ancata-101 | Ancata-124 |
|---|---|---|---|
| $k_{cat}^{pyruvate}(s^{-1})$ | 0.50 ± 0.01 | 1.50 ± 0.03 | 0.74 ± 0.03 |
| $K_m^{pyruvate}$(mM) | 0.23 ± 0.02 | 1.15 ± 0.02 | 0.93 ± 0.01 |
| $k_{cat}/K_m^{pyruvate}$(L/(s · mmol)) | 2.22 | 1.30 | 0.79 |
| $k_{cat}^{\alpha\text{-}MBA}(s^{-1})$ | 0.64 ± 0.01 | 1.07 ± 0.02 | 0.60 ± 0.01 |
| $K_m^{\alpha\text{-}MBA}$(mM) | 0.23 ± 0.03 | 0.28 ± 0.03 | 0.28 ± 0.01 |
| $k_{cat}/K_m^{\alpha\text{-}MBA}$(L/(s · mmol)) | 2.82 | 3.81 | 2.07 |

(6) Determination of Thermal Stability.

1) Determination of $T_{50}^{10}$ $T_{50}^{10}$ is the temperature when the residual enzyme activity is reduced to 50% after incubation of the pure enzyme at 4-60'C for 10 min. The purified wild enzyme and its mutants were incubated at 4° C., 25° C., 30° C., 35° C., 40° C., 45° C., 47° C., 49° C., 50° C. and 55° C. for 10 min, then placed on ice to cool down for 10 min immediately after incubation, then the residual activity of the wild type and its mutants were determined. The $T_{50}^{10}$ of the wild type and the mutants were calculated by using the temperature as the horizontal coordinate and the ratio of enzyme activity between heat-treated enzyme and untreated enzyme as the vertical coordinate and plotting using Origin 8.0 software.

2) Determination of $t_{1/2}$ $t_{1/2}$ is the time when the residual enzyme activity decreases to 50% after incubation of the pure enzyme at 40° C. for different times. The purified wild type and its mutants were incubated at 40° C. for 0-24 hours. After incubation, the wild type and its mutants were immediately cooled on ice for 10 min, and the residual activity of the wild type and its mutants were measured. $t_{1/2}$ of the wild type and the mutants at 40° C. were calculated using time as horizontal coordinate and the ratio of enzyme activity between heat-treated enzyme and untreated enzyme as the vertical coordinate and plotting using Origin 8.0 software.

TABLE 3

Stability parameters of wild type and mutants

| Name | WT-AT | Ancata-101 | Ancata-124 |
|---|---|---|---|
| $T_{50}^{10}$ (° C.) | 37.89 ± 0.5 | 49.00 ± 0.4 | 49.03 ± 0.5 |
| Increased temperature of $T_{50}^{10}$ (° C.) | — | 11.11 | 11.14 |
| $t_{1/2}$ (min) | 6.90 ± 0.6 | >1440 | >1440 |
| Increase fold of $t_{1/2}$ | — | 207 | 207 |

Figure 3:
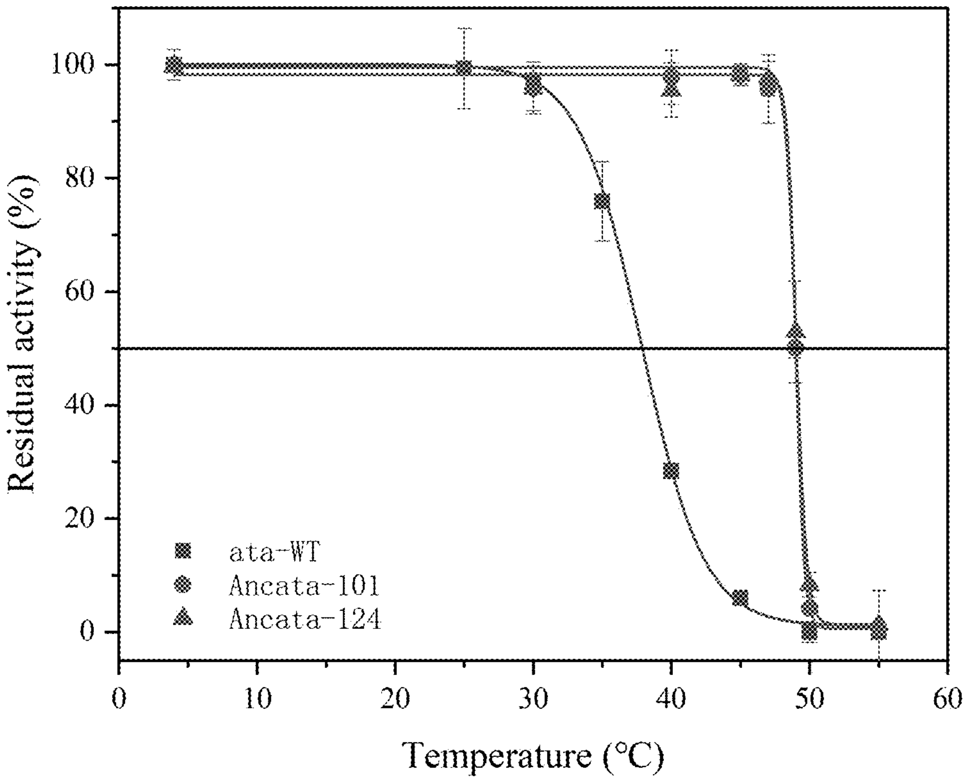
FIG. 3 is the result of stability assay of wild-type ω-transaminase and ω-transaminase mutant enzymes; in which, a is $T_{50}^{10}$ between wild-type and Ancata-101 and Ancata-124; b is $t_{1/2}$ of wild-type, Ancata-101 and Ancata-124 at 40° C., 45° C. and 47° C.
Figure 3:
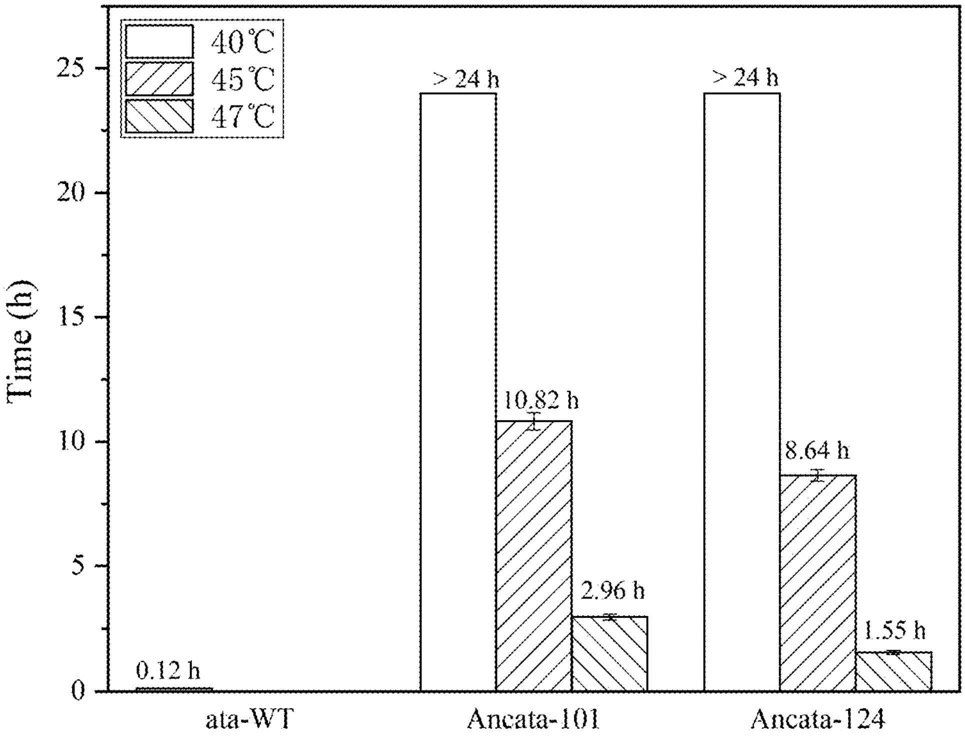

The stability measurements of mutants Ancata-101 and Ancata-124 are shown in FIG. 3 and Table 3. The $T_{50}^{10}$ of the wild type was 37.89° C., and the $T_{50}^{10}$ of mutants Ancata-101 and Ancata-124 were 49.00° C. and 49.03° C., respectively, which were 11.11° C. and 11.14° C. higher than that of the wild type, respectively. $t_{1/2}$ of mutants Ancata-101 and Ancata-124 were both greater than 24 hours (1440 min), while the wild-type $t_{1/2}$ was only 6.90 min. At 45° C., the residual activity of the wild-type enzyme decreased to 50% after incubation for less than one minute, while the residual activity of the two mutants was still greater than 50% after over 6 h of incubation.

(7) Determination of Substrate Spectrum

The catalytic reaction was performed with (R)-α-MBA as amine group donor and benzaldehyde, acetophenone, 4-fluoroacetophenone, 4-chloroacetophenone, 4-bromoacetophenone, 4-methoxyacetophenone, 4-methylacetophenone, 4-trifluoromethylacetophenone, 4-nitroacetophenone, 1-acetylnaphthalene, 2-acetylnaphthalene, α-tetralone as amino group acceptors. 2 mL reaction system comprised 10 mmol/L (R)-α-MBA, 10 mmol/L each ketone substrate, 0.1 mmol/L PLP, 50 mmol/L PBS (pH 8.0), and 0.15 mg/mL pure enzyme solution. The amount of each product produced was determined by HPLC after 24 h of reaction at 30° C. and 40° C. and 180 r/min, and yield and e.e. values of the product were calculated.

HPLC detection method: The reaction solution was filtered through a 0.22 μm filter membrane and then detected by HPLC on Agilent InfinityLab Poroshell 120 EC-C18 column (4.6×150 mm, 4.0 μm) with mobile phase being acetonitrile:water=40:60 (v/v) at a flow rate of 1.0 mL/min. The UV detection wavelength was 210 nm.

To verify the catalytic performance of the ancestral enzymes Ancata-101 and Ancata-124 for different substrates, the enzyme-catalyzed reactions of WT, Ancata-101 and Ancata-124 were carried out at 10 mmol/L of each substrate concentration, and the results are shown in Tables 4 and 5. After 24 hours of reaction, except for benzylamine generated from benzaldehyde, Ancata-101 and Ancata-124 showed elevated yields compared to WT for the remaining nine substrates catalyzed, and all the products produced were in strict R-configuration (e.e. >99.5%) except for benzaldehyde which produced the corresponding product. In contrast to WT, which catalyzed various substrates (except benzaldehyde and 4-nitroacetophenone) in lower yields at 40° C. than at 30° C., both ancestral enzymes obtained higher catalytic yields at 40° C. than at 30° C. Overall the ancestral enzymes Ancata-101 and Ancata-124 showed better catalytic activity for aromatic ketone substrates than WT.

TABLE 4

Parameters of substrate profiles of wild type and mutants at 30° C.

| Substrate | WT Yield (%) | Ancata-101 Yield (%) | Ancata-124 Yield (%) |
|---|---|---|---|
| Benzaldehyde | 69.4 | 57.8 | 61.6 |
| 4-Fluoroacetophenone | 20.6 | 4.2 | 4.4 |
| 4-Chloroacetophenone | 30.8 | 30.1 | 26.6 |
| 4-Bromoacetophenone | 29.6 | 29.4 | 29.6 |
| 4-Methylacetophenone | 15.5 | 2.6 | 7.2 |
| 4-Methoxyacetophenone | 6.1 | 6.8 | 1.7 |
| 4-Trifluoromethylacetophenone | 36.0 | 30.8 | 33.8 |
| 4-Nitroacetophenone | 42.9 | 45.9 | 42.5 |
| 1-Acetyl Naphthalene | 38.5 | 42.2 | 42.6 |
| 2-Acetyl Naphthalene | 24.5 | 24.1 | 26.0 |

TABLE 5

Parameters of substrate profiles of wild type and mutants at 40° C.

| Substrate | WT Yield (%) | Ancata-101 Yield (%) | Ancata-124 Yield (%) |
|---|---|---|---|
| Benzaldehyde | 79.1 | 77.3 | 73.5 |
| 4-Fluoroacetophenone | 13.9 | 28.4 | 29.0 |
| 4-Chloroacetophenone | 16.0 | 37.5 | 34.9 |
| 4-Bromoacetophenone | 16.4 | 33.7 | 32.6 |
| 4-Methylacetophenone | 5.7 | 22.9 | 24.3 |
| 4-Methoxyacetophenone | 2.9 | 8.3 | 12.3 |
| 4-Trifluoromethylacetophenone | 32.6 | 39.9 | 38.4 |
| 4-Nitroacetophenone | 47.7 | 52.2 | 36.3 |
| 1-Acetyl Naphthalene | 16.0 | 44.5 | 44.6 |
| 2-Acetyl Naphthalene | 22.0 | 28.2 | 29.5 |

(8) Whole-Cell Catalytic System Construction

The catalytic reaction was carried out using 1-(R)-phenylethylamine as amine group donor and 1-acetylnaphthalene as amino group acceptor. 10 mL of the reaction system comprised 10 mmol/L 1-(R)-phenylethylamine, 10 mmol/L each ketone substrate, 0.1 mmol/L PLP, 50 mmol/L PBS (pH 8.0), and 10 g/L ω-transaminase wet bacteria. After reaction for 15 hours at 40° C. and 180 r/min, the amount of each product produced was determined by HPLC and the yield and e.e. values of the products were calculated.

HPLC detection method: The reaction solution was filtered through a 0.22 μm filter membrane and then detected by HPLC on Agilent InfinityLab Poroshell 120 EC-C18 column (4.6×150 mm, 4.0 μm) with mobile phase being acetonitrile:water=40:60 (v/v) at a flow rate of 1.0 mL/min. The UV detection wavelength was 210 nm.

Figure 4:
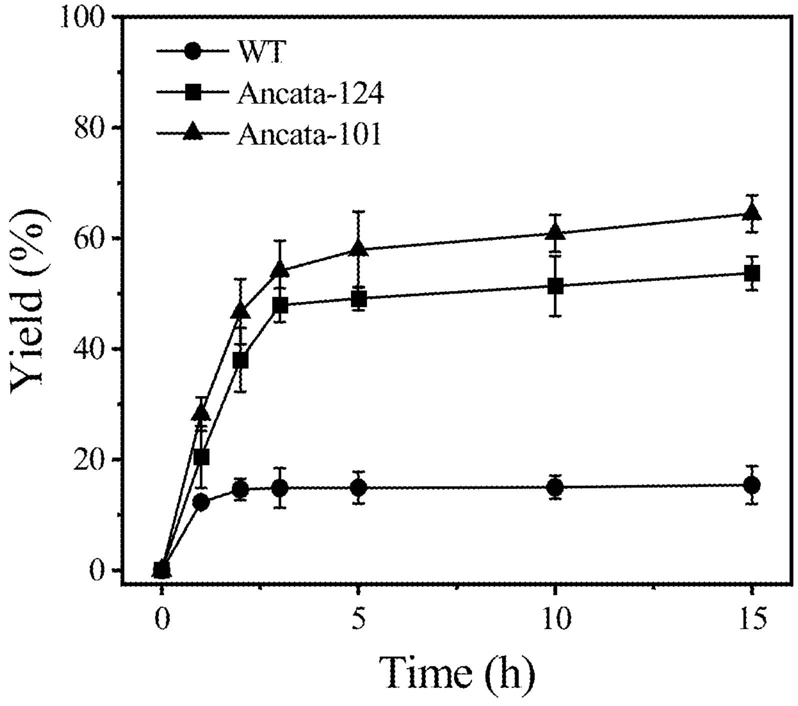
FIG. 4 is the result of whole-cell catalytic production of 1-(R)-naphthylethylamine by wild-type ω-transaminase and ω-transaminase mutant enzymes.

As shown in the whole-cell catalytic results in FIG. 4, the transaminase mutants Ancata-101 and Ancata-124 could catalyze 1-acetylnaphthalene at 40° C. for more than 15 hours, which was significantly longer than the wild-type catalyzing time of 1 hour. Among them, the ancestral enzyme Ancata-101 was able to achieve more than 60% conversion at a catalytic temperature of 40° C. Overall, whole-cell catalytic experiments could show that the ancestor enzymes with greatly improved thermal stability could greatly extend the catalytic time and increase the catalytic efficiency.

Applicant hereby electronically submits the amended Sequence Listing in XML (CRF format) with the file name of USSN18287879_SEQ_LIST.XML, created on Sep. 6, 2024 and with the size of 10,229 bytes. The replacement "Sequence Listing XML" does not include new matter.

What is claimed is:

1. An ω-transaminase mutant based on ancestral sequence reconstruction, wherein the ω-transaminase mutant is derived from mutation of ω-transaminase from *Aspergillus terreus*, and the ω-transaminase mutant has the amino acid sequence of SEQ ID NO. 4 or SEQ ID NO. 6.

2. A gene encoding the ω-transaminase mutant of claim 1.

3. The gene of claim 2, wherein the ω-transaminase mutant has the gene sequence of SEQ ID NO. 3 or SEQ ID NO. 5.

4. A recombinant expression plasmid, comprising the gene of claim 3.

5. A genetically engineered bacterium, comprising the recombinant expression plasmid of claim 4.

6. A method for catalyzing generation of acetophenone from (R)-(+)-α-methylbenzylamine, wherein acetophenone is generated by a transamination reaction, using (R)-(+)-α-methylbenzylamine and pyruvic acid as substrates and catalyzed by the ω-transaminase mutant of claim 1.

7. A method for catalyzing generation of acetophenone from (R)-(+)-α-methylbenzylamine, wherein acetophenone is generated by a transamination reaction, using (R)-(+)-α-methylbenzylamine and pyruvic acid as substrates and catalyzed by the genetically engineered bacterium of claim 5.

* * * * *

SEQUENCE LISTING

```
Sequence total quantity: 6
SEQ ID NO: 1          moltype = DNA  length = 978
FEATURE               Location/Qualifiers
source                1..978
                      mol_type = genomic DNA
                      organism = Aspergillus terreus
SEQUENCE: 1
atggccagta tggataaggt ttttgcaggc tatgctgccc gtcaagcaat cttagaaagt  60
accgaaacta cgaacccgtt tgccaaagga attgcctggg tcgaagggga actcgttcct  120
ttagctgaag cacgcattcc actcctcgat cagggcttca tgcactccga tctgacctac  180
```

-continued

```
gacgtaccgt ctgtttggga tggcgatttt tttcgtttag atgatcatat tacacgcctg  240
gaagcaagct gcaccaagct gaggctgcgt ctacccttac cacgtgatca agttaaacaa  300
atcctggtgg aaatggtcgc aaaatctggt attcgggatg catttgttga attgatagtc  360
acccgcggtc ttaaaggggt gcgaggaact cgtccgcatg atatagtgaa caacctgtac  420
atgtttgtgc agccgtacgt gtgggttatg gagccggata tgcagcgcgt aggcggcagc  480
gcagtggtgg ctaggaccgt ccgccgggta ccaccgggcg ctattgatcc gaccgtcaag  540
aatcttcagt ggggtgatct tgttcgtgga atgtttgaag cggctgatcg tggcgcaaca  600
tatcccttcc ttaccgacgg cgatgcgcac ctgactgaag gatcgggttt taatatagta  660
ttagtcaaag atggcgtcct gtatacgcca gatcgcgggg tgctgcaggg agtgactcgc  720
aagtccgtta tcaacgctgc tgaagccttt ggaatagaag tgcgggttga gttcgttcca  780
gttgagctgg cctaccggtg tgacgagatt ttcatgtgca cgacggcggg tggcattatg  840
cctatcacaa cattggacgg tatgcctgta aatggtgggc aaattgggcc tattacgaaa  900
aaaatatggg acggttattg ggcgatgcat tatgacgccg cgtattcgtt cgagatcgac  960
tataatgaga gaaattag                                                978

SEQ ID NO: 2           moltype = AA  length = 326
FEATURE                Location/Qualifiers
source                 1..326
                       mol_type = protein
                       organism = Aspergillus terreus
SEQUENCE: 2
MASMDKVFAG YAARQAILES TETTNPFAKG IAWVEGELVP LAEARIPLLD QGFMHSDLTY  60
DVPSVWDGRF FRLDDHITRL LEASCTKLRL RLPLPRDQVK QILVEMVAKS GIRDAFVELI  120
VTRGLKGVRG TRPEDIVNNL YMFVQPYVWV MEPDMQRVGG SAVVARTVRR VPPGAIDPTV  180
KNLQWGDLVR GMFEAADRGA TYPFLTDGDA HLTEGSGFNI VLVKDGVLYT PDRGVLQGVT  240
RKSVINAAEA FGIEVRVEFV PVELAYRCDE IFMCTTAGGI MPITTLDGMP VNGGQIGPIT  300
KKIWDGYWAM HYDAAYSFEI DYNERN                                       326

SEQ ID NO: 3           moltype = DNA  length = 990
FEATURE                Location/Qualifiers
source                 1..990
                       mol_type = other DNA
                       organism = synthetic construct
SEQUENCE: 3
atggcgagca tggaaaaagt gtttgcgggc tatcaggcgc gccaggcggt gctggaagcg  60
agcgcgagca ccaacccgtt tgcgaaaggc attgcgtggg tggaaggcga actggtgccg  120
ctgcatgaag cgcgcattcc gctgctggat cagggcttta tgcatagcga tctgacctat  180
gatgtgccga gcgtgtggga tggccgcttt tttcgcctgg atgatcatct gagccgcctg  240
gaagcgagct gcagcaaaat gcgcctgaaa ctgccgctgc cgcgcgaaga agtgaaacag  300
attctggtgg atatggtggc gaaaagcggc attcgcgatg cgtttgtgga actgattgtg  360
acccgcggcc tgaaaggcgt gcgcggcagc aaaccggaag aactggtgaa caacaacctg  420
tatatgttta ttcagccgta tgtgtgggtg atggaaccgg aaatgcagcg caccggcggc  480
agcgcgatta ttgcgcgcac cgtgcgccgc gtgccgccgg gcagcatgga tccgaccgtg  540
aaaaacctgc agtggggcga tctgacccgc ggcatgtttg aagcgagcga tcgcggcgcg  600
acctatccgt ttctgaccga tggcgatgcg aacctgaccg aaggcagcgg ctttaacatt  660
gtgctggtga aagatggcgt gctgtatacc ccggatcgcg gcgtgctgga aggcgtgacc  720
cgcaaaagcg tgattgatgt ggcgcgcgcg aacggcattg aagtgcgcgt ggaagtggtg  780
ccggtggaac tggcgtatca gtgcgatgaa atttttatgt gcaccaccgc gggcggcatt  840
atgccgatta ccagcctgga tggcaaaccg gtgaacgatg gcaaagtggg cccgattacc  900
aaaaaaattt gggatggcta ttgggcgatg cattatgatc cggcgtatag ctttgaaatt  960
gattatgaaa gcgcgagcaa aaaaagcggc                                   990

SEQ ID NO: 4           moltype = AA  length = 330
FEATURE                Location/Qualifiers
source                 1..330
                       mol_type = protein
                       organism = synthetic construct
SEQUENCE: 4
MASMEKVFAG YQARQAVLEA SASTNPFAKG IAWVEGELVP LHEARIPLLD QGFMHSDLTY  60
DVPSVWDGRF FRLDDHLSRL EASCSKMRLK LPLPREEVKQ ILVDMVAKSG IRDAFVELIV  120
TRGLKGVRGS KPEELVNNNL YMFIQPYVWV MEPEMQRTGG SAIIARTVRR VPPGSMDPTV  180
KNLQWGDLTR GMFEASDRGA TYPFLTDGDA NLTEGSGFNI VLVKDGVLYT PDRGVLEGVT  240
RKSVIDVARA NGIEVRVEVV PVELAYQCDE IFMCTTAGGI MPITSLDGKP VNDGKVGPIT  300
KKIWDGYWAM HYDPAYSFEI DYESASKKSG                                   330

SEQ ID NO: 5           moltype = DNA  length = 984
FEATURE                Location/Qualifiers
source                 1..984
                       mol_type = other DNA
                       organism = synthetic construct
SEQUENCE: 5
atggccagca tggaaaaagt gtttgccggt tatcaggccc gtcaggccgt tctggaagca  60
agcgcaagta ccaatccgtt tgcaaaaggc attgcctggg tggaaggcga actggttccg  120
ctgcatgaag cacgtattcc gctgctggat cagggcttta tgcatagtga tctgacctat  180
gatgttccga gcgtgtggga tggccgcttt ttccgtctgg atgatcatct gagtcgtctg  240
gaagcatcat gcgccaaact gcgcctgaaa ctgccgctgc cgcgtgaaga agttaaacag  300
attctggttg atatggtggc aaaaagtggt attcgtgatg catttgtgga actgattgtg  360
acccgcggcc tgaaaggtgt tcgtggtagc aaaccggaag atctggtgaa taataatctg  420
tatatgttca tccagccgta tgtgtgggtt atggaaccgg aagttcagcg caccggcggt  480
```

-continued

```
agcgccatta ttgcacgtac cgttcgtcgt gtgccgccgg gcgctattga tccgaccgtt  540
aaaaatctgc agtggggtga cctggttcgc ggcatgtttg aagccagcga tcgtggcgca  600
acctatccgt ttctgaccga tggtgacgca aatctgaccg aaggtagtgg ctttaatatt  660
gtgctggtga aagatggtgt tctgtatacc ccggatcgtg gcgttctgga aggcgtgacc  720
cgcaaaagtg tgattgatgt tgcacgcgcc aatggtattg aagtgcgcgt tgaagtggtg  780
ccggtggaaa tggcatatca gtgtgatgaa atttttatgt gcaccaccgc cggcggcatt  840
atgccgatta ccagtctgga tggtaaaccg gtgaatgatg gcaaagttgg cccgattacc  900
aaaaagattt gggatggcta ttgggccatg cattatgatc cggcatatag ttttgaaatt  960
gattatgaaa gcgcgagtaa aagt                                         984

SEQ ID NO: 6           moltype = AA  length = 328
FEATURE                Location/Qualifiers
source                 1..328
                       mol_type = protein
                       organism = synthetic construct
SEQUENCE: 6
MASMEKVFAG YQARQAVLEA SASTNPFAKG IAWVEGELVP LHEARIPLLD QGFMHSDLTY  60
DVPSVWDGRF FRLDDHLSRL EASCAKLRLK LPLPREEVKQ ILVDMVAKSG IRDAFVELIV  120
TRGLKGVRGS KPEDLVNNNL YMFIQPYVWV MEPEVQRTGG SAIIARTVRR VPPGAIDPTV  180
KNLQWGDLVR GMFEASDRGA TYPFLTDGDA NLTEGSGFNI VLVKDGVLYT PDRGVLEGVT  240
RKSVIDVARA NGIEVRVEVV PVEMAYQCDE IFMCTTAGGI MPITSLDGKP VNDGKVGPIT  300
KKIWDGYWAM HYDPAYSFEI DYESASKS                                     328
```